United States Patent [19]
Sanvordeker et al.

[11] Patent Number: 4,900,552
[45] Date of Patent: Feb. 13, 1990

[54] MUCOADHESIVE BUCCAL DOSAGE FORMS

[75] Inventors: Dilip R. Sanvordeker, Irvine; Sau-Hung S. Leung, Corona, both of Calif.

[73] Assignee: Watson Laboratories, Inc., Corona, Calif.

[21] Appl. No.: 175,075

[22] Filed: Mar. 30, 1988

[51] Int. Cl.$^4$ ............................................. A61F 7/02
[52] U.S. Cl. .................................... 424/422; 424/435
[58] Field of Search ............... 424/435, 434, 422, 447, 424/448, 468

[56] References Cited
U.S. PATENT DOCUMENTS 307,537 11/1884 Foulks .................................. 424/435
3,598,122 8/1971 Zaffaroni ............................. 424/435

Primary Examiner—Nancy Swisher
Attorney, Agent, or Firm—Dressler, Goldsmith, Shore, Sutker & Milnamow, Ltd.

[57] ABSTRACT

A trilaminate film suitable for prolonged and sustained delivery of an active ingredient in a buccal cavity is disclosed. A hydratable mucoadhesive base layer, a non-adhesive reservoir layer and a water-impermeable carrier film sandwiched between and bonded to the base layer and the reservoir layer are the elements which form the trilaminate film.

10 Claims, 2 Drawing Sheets

U.S. Patent  Feb. 13, 1990  Sheet 1 of 2  4,900,552
Fig-1-
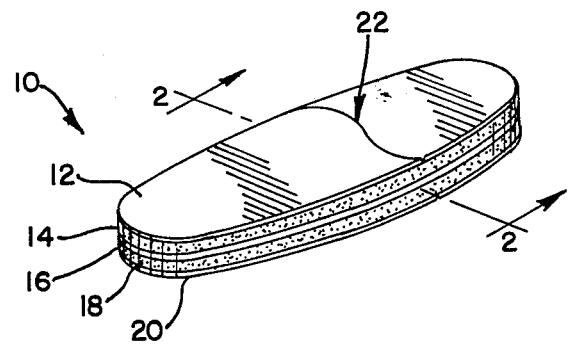
Fig-2-
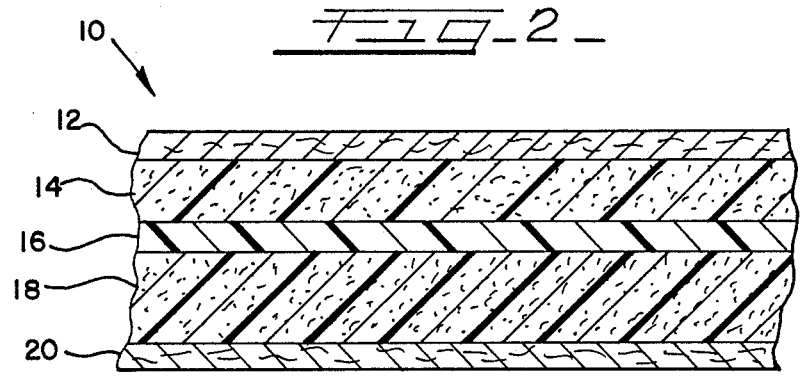

MUCOADHESIVE BUCCAL DOSAGE FORMS

TECHNICAL FIELD

This invention relates to a buccal dosage form, and in particular to a mucoadhesive trilaminate suitable for prolonged/sustained delivery of an active ingredient in the buccal cavity.

BACKGROUND OF THE INVENTION

Delivery of drugs by the buccal route of administration and therapeutic compositions and methods therefor are well known. U.S. Patent No. 4,615,697 to Robinson provides an excellent review of this subject. The buccal delivery systems disclosed in Robinson utilize known bioadhesives to hold the system in place in the buccal cavity after insertion therein. The drug is released from a bioadhesive matrix and absorbed into the buccal lining and provides a means of trans-mucosal delivery of therapeutic agents that are subject to poor bioavailability due to solubility limitations, polarity considerations, degradation due to pH, enzymatic exposure or "first pass" metabolism by the liver or gastrointestinal enzymes after oral ingestion. However, such delivery systems, when used with a backing, have a tendency to distort or curl upon hydration due to the different rates of hydration of the several layers that are present. Also, the drug present is not released into the buccal cavity.

The buccal cavity is susceptible to many ailments which require sustained treatment, however. To that end, it would be desirable to release an active ingredient in the buccal cavity itself for an extended period of time. The present invention provides a means for accomplishing this purpose.

SUMMARY OF THE INVENTION

The present invention contemplates a buccal dosage form which is a trilaminate film segment capable of delivering an active ingredient within the buccal cavity while attached to a wall of that cavity. The trilaminate film segment includes a hydratable mucoadhesive base layer, a non-adhesive reservoir layer and a water-impermeable barrier sandwiched between and bonded to the base layer and the reservoir layer.

The mucoadhesive base layer comprises a hydratable mucoadhesive polymeric matrix. The reservoir layer includes a plasticized film-forming cellulose ester, a dehydrated hydrogel and an active ingredient. The water-impermeable barrier film includes a cellulose ester film.

Numerous other advantages and features of the present invention will become readily apparent from the following detailed description of the invention, the accompanying drawings and the appended claims.

BRIEF DESCRIPTION OF THE DRAWING

In the drawings:
FIG. 1 is a perspective view of a trilaminate film segment with release liners embodying the present invention;
FIG. 2 is an enlarged fragmentary sectional view of the trilaminate film segment with release liners of FIG. 1 taken along plane 2-2 in FIG. 1.

DETAILED DESCRIPTION OF THE INVENTION

Figure 3:
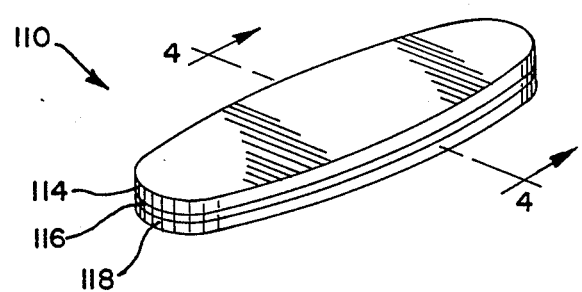
FIG. 3 is a perspective view of a trilaminate film segment without release liners embodying the present invention.

While this invention is susceptible to embodiment in many different forms, preferred embodiments of the invention are shown. It should be understood, however, that the present disclosure is to be considered as an exemplification of the principles of this invention and is not intended to limit the invention to the embodiments illustrated.

Referring to FIGS. 1 and 2, an oblong segment 10 of a trilaminate film is constituted by water-impermeable barrier layer 16 sandwiched between and bonded to hydratable mucoadhesive base layer 18 and non-adhesive reservoir layer 14. While FIG. 1 shows an oblong shape, any shape that fits comfortably within the buccal cavity is suitable. Protective release layers 12 and 20 are removably secured to the non-adhesive reservoir layer 14 and the hydratable mucoadhesive base layer 18, respectively. The protective release layers 12 and 20 each may have a score line such as line 22 to allow easy removal. In use, the protective release layers 12 and 20 are removed and the trilaminate film 10 placed within the buccal cavity with the hydratable mucoadhesive base layer 18 adhering to the lining of the buccal cavity. If desired, the individual layers may be color coded.

Figure 4:
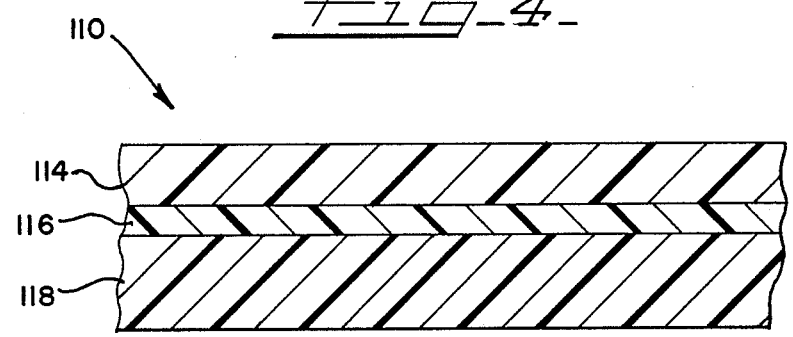
FIG. 4 is an enlarged fragmentary sectional view of the trilaminate film segment without release liners of FIG. 3 taken along plane 3—3 in FIG. 3.

Referring to FIGS. 3 and 4, an embodiment of an oblong segment 110 of a trilaminate film without the release layers of FIGS. 1 and 2 is shown. The oblong segment 110 is constituted by water-impermeable barrier layer 116 sandwiched between and bonded to hydratable mucoadhesive base layer 118 and non-adhesive reservoir layer 114. While FIGS. 3 shows an oblong shape, any shape that fits comfortably within the buccal cavity is suitable.

The dosage form can be packaged in unit dose blister packs, pouches in a carton, vials with screw or flip-top lids, bottles with screw or flip-top lids, or any other convenient package form.

The dosage form can be prepared using a variety of coating, laminating and converting processes and equipment for each layer. Coating solutions of the various layers are prepared using pharmaceutically acceptable non-aqueous solvents as further described hereinbelow.

A variety of coating methods such as Mayer rod, gravure, and knife-over-roll can be used to coat and oven-dry a base layer and subsequent additional film layers on the base layer. The dried trilaminate film can be processed using converting equipment to die cut trilaminate buccal dosage forms of suitable size and shape. Optionally, the trilaminate film can be on a release liner and covered with a second release liner prior or subsequent to processing.

The term mucoadhesive, as used herein, is a material that adheres to a mucosal tissue surface in-vivo and/or in-vitro upon hydration. Such adhesion will adherently localize the dosage form onto the mucus membrane and requires the application of a force of at least about 50 dynes/cm$^2$ to separate the mucoadhesive material from the mucus membrane.

Several types of materials are suitable for forming the hydratable mucoadhesive base layer. One type of material is a water-swellable, but water-insoluble fibrous, cross-linked carboxy-functional polymer. The polymer contains a plurality of a repeating unit of which at least about 80 percent contain at least one carboxyl functionality and about 0.05 to about 1.5 percent cross-linking agent substantially free from polyalkenyl polyether, with the percentages being based upon the weights of the unpolymerized repeating unit and cross-linking agent, respectively. In more preferred practice, at least about 90 percent of the repeating units contain at least one carboxyl functionality, and in still more preferred practice, at least 95 percent of those repeating units contain at least one carboxyl functionality. Most preferably, this mucoadhesive material is a reaction product of the polymerization of only a carboxyl-functional monomer and a cross-linking agent. Also in more preferred practice, this mucoadhesive contains about 0.1 to about 1 percent by weight of polymerized cross-linking agent. This type of mucoadhesive polymer is disclosed in U.S. Patent No. 4,615,697 to Robinson, and is commercially available under the generic name "polycarbophil".

Other optional mucoadhesives include polymers which are hydrophilic and water-dispersible, have free carboxylic groups and a relatively high base binding capacity. Preferred polymers include water dispersible polycarboxylated vinyl polymers. Polyacrylic acid polymers are particularly preferred. The average number molecular weight of this polymer is desirably between about 1,250,000 and 3,000,000. Suitable polyacrylic acid polymers include, but are not limited to, polyacrylic acid polymers lightly crosslinked with a polyalkenyl polyether such as those commercially available from B. F. Goodrich, Cincinnati, Ohio, under the trademarks Carbopol® 434,934P, 940 and 941.

Also suitable as the mucoadhesive are hydrophilic polysaccharide gums such as natural plant exudates, e.g., jaraya gum, ghatti gum and the like, as well as seed gums, e.g., guar gum, locust bean gum, psillium seed gum and the like.

Cross-linked alginate gum gel of the type described in U.S. Patent No. 3,640,741 to Etes are also suitable for use as the mucoadhesive.

Upon contact with mucus which is excreted by the lining of the buccal cavity, the mucoadhesive hydrates thus adhering the buccal dosage form to the lining.

The mucoadhesive base layer may also include a medicinal agent for systemic delivery, if desired.

In addition to the active ingredient, the non-adhesive reservoir layer is constituted by a plasticized film-forming cellulose ester and a dehydrated hydrogel. The relative amounts of the cellulose ester and the dehydrated hydrogel are balanced to maintain the reservoir layer non-adhesive when it is hydrated within the buccal cavity while providing a rate of hydration for the reservoir layer that substantially matches the rate of hydration of the mucoadhesive base layer. In this manner, undesirable curling of the buccal dosage form upon use is avoided. The cellulose ester and the dehydrated hydrogel can be present in the non-adhesive reservoir layer in a weight ratio in the range of about 7:3 to about 1:4, respectively, and preferably in the range of about 6:4 to about 1:3. In general, the exposed surface of the reservoir substantially minimize friction and avoid erosion of the mucus membrane in contact therewith.

Suitable film-forming cellulose esters for the present purposes are cellulose acetate butyrate, cellulose acetate isobutyrate, cellulose acetate propionate, cellulose acetate, and the like.

Hydrogels are water-swollen networks of hydrophilic copolymers or homopolymers and may be neutral hydrogels, ionic hydrogels, or swollen interpenetrating polymeric networks. A "dehydrated hydrogel," as the term is used herein and in the appended claims is a hydrogel that contains less than its equilibrium value of water and thus is swellable when placed in an aqueous environment.

Suitable dehydrated hydrogels for the purposes of the present invention are those derived from polyoxyalkylene block copolymers, hydroxyethyl methacrylate homopolymers, hydroxyethoxyethyl methacrylate homopolymers, hydroxydiethoxyethyl methacrylate homopolymers, methoxyethyl methacrylate homopolymers, methoxydiethoxyethyl methacrylate homopolymers, ethylene glycol dimethacrylate hompolymers, N-vinyl-2-pyrrolidone homopolymers (PVP), methacrylic acid hompolymers, vinyl acetate homopolymers, copolymers of the foregoing monomers, alginic acid, poly(ethylene oxide)/propylene oxide copolymers with alginic acid, polyvinyl alcohol, and the like.

A particularly preferred polyoxyalkylene block copolymer for the present purpose is a polyoxyethylene-polyoxypropoylene block copolymer commercially available under the designation Poloxamer [its Cosmetic, Toiletry and Fragrance Association, Inc. (CTFA) name]. Illustrative of the above block copolymer are Pluronic® F-127 or Pluronic® F-68 (both commercially available from BASF Wayandotte Corporation, Parsippany, New Jersey). The aforementioned block copolymer is represented by the formula:

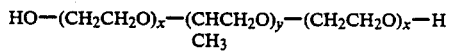

wherein x and y are alike or different and are whole integers having a value of about 2 to about 128 for the x moiety and about 16 to about 67 for the y moiety. The foregoing type of block copolymer has water-soluble oxyethylene chains on both ends of the block and a water-insoluble oxypropylene chain in a center of the block. The weight ratio of oxyethylene chains to oxypropylene chains in the copolymer is about 7:3. The combination of polyoxyalkylene block copolymer with alginic acid, preferably in a weight ratio of about 5 to about 0.2, respectively, is particularly well suited as a water-swellable hydrogel system.

Suitable plasticizers for the non-adhesive reservoir layer are 1,2,3-propanetiol triacetate, distilled acetylated monoglycerides, sucrose acetate isobutyrate, and the like. The plasticizer can serve the additional function as a carrier of the active ingredient.

Optional constituents that can be present in the non-adhesive reservoir layer are pigments, opacifiers, and the like.

Illustrative active ingredients that can be present in the reservoir layer include breath fresheners and flavors, e.g., spearmint oil, peppermint oil, cinnamaldehyde, cetyl pyridinium chloride, menthol saccharin sodium, glycyrrhizin, malt syrup, citric acid, tartaric acid, lemon oil, citrus flavor, and the like, sodium fluoride and the like, anti-plaque/anti-bacterial compositions suitable to treat or prevent periodontal disease, e.g., chlorobutanol, chlorothymol, chlorohexidine, their salts, and the like, dental pain control ingredients, e.g., benzocaine, lidocaine and the like.

In addition to the above ingredients, there may also be incorporated other additives selected from among the various pharmaceutically acceptable additives available to the those skilled in the art for the purpose of obtaining desirable processing and physical qualities including enhancement of the dispersibility and stability of the active ingredient. Such additives which can be used in addition to the active ingredient include the following substances: stabilizers/preservatives, e.g., parahydroxybenzoic acid alkyl esters, antioxidants, antifungal agents, and the like; coloring agents, e.g., aluminum lake, titanium dioxide, and the like; excipients/disintegration modulating agents, e.g., magnesium silicate, silicic acid anhydride, aluminum silicate, calcium carbonate, magnesium aluminum metasilicate, calcium hydrogen phosphate, and the like; stearic acid and its salts; palmitic acid; talc; and other substances known as emulsifiers, dispersants, binders, thickeners and the like.

The water-impermeable barrier is a cellulose ester film. The barrier inhibits diffusion of the active ingredient to the base layer. Suitable cellulose esters for this purpose are cellulose acetate butyrate, cellulose acetate isobutyrate, cellulose acetate propionate and the like. A pigment such as titanium dioxide and/or plasticizers such as distilled acetylated monoglycerides, (Myvacet ®, commercially available from Eastman Chemical Products, Inc., Kingston, Tennessee) or sucrose acetate isobutyrate, (Eastman ® SAIB-90 or SAIB-90SG, commercially available from Eastman Chemical Products, Inc., Kingston, Tennessee) can also be present if desired.

The present invention is further illustrated by the following examples.

EXAMPLE 1:

Fabrication of the mucoadhesive buccal dosage form.

Four mucoadhesive buccal dosage forms were fabricated using different compositions for the reservoir layer and the base layer, all prepared using a solvent solution of ethyl acetate:acetone:isopropanol in a weight ratio of 5:4:1, respectively. Other ratios of the said solvents or combinations of other pharmaceutically acceptable solvents that dissolve the said cellulosic film forming polymers and the plasticizers may be used, however, if desired. The fabricated dosage forms are tabulated in Table I, below.

TABLE I

Mucoadhesive Buccal Dosage Form Compositions For Sustained Delivery Containing Breath Freshening Agents

| Component, (grams) | C1 | | | C2 | | | C3 | | | C4 | | |
|---|---|---|---|---|---|---|---|---|---|---|---|---|
| | $A^1$ | $M^2$ | $B^2$ | $A^1$ | $M^2$ | $B^2$ | $A^1$ | $M^2$ | $B^2$ | $A^1$ | $M^2$ | $B^2$ |
| Cellulose acetate butyrate[4] | 3.25 | 7.0 | 2.0 | 3.25 | 7.0 | 2.0 | 3.25 | 7.0 | 2.0 | 3.25 | 7.0 | 2.0 |
| Triacetin | 2.00 | — | 2.0 | 2.00 | — | 2.0 | 2.00 | — | 2.0 | 2.00 | — | 2.0 |
| Polyvinyl pyrrolidone[5] | 2.00 | — | 1.0 | 2.00 | — | 1.0 | 2.00 | — | 1.0 | 2.00 | — | 1.0 |
| Solvent solution[6] | 30.00 | 30.0 | 30.0 | 30.00 | 30.0 | 30.0 | 30.00 | 30.0 | 30.0 | 30.00 | 30.0 | 30.0 |
| Colorant[8] | 0.01 | — | — | 0.01 | — | — | 0.01 | — | — | 0.01 | — | — |
| Titanium (IV) dioxide | — | 2.0 | — | — | 2.0 | — | — | 2.0 | — | — | 2.0 | — |
| Sucrose acetate isobutyrate[7] | — | 1.4 | — | — | 1.4 | — | — | 1.4 | — | — | 1.4 | — |
| Polycarbophil[9] | — | — | 6.0 | — | — | 3.0 | — | — | — | — | — | 6.0 |
| Alginic acid[10] | 7.00 | — | — | 7.00 | — | — | 7.00 | — | — | — | — | — |
| Flavoring[11] | 5.00 | — | — | 5.00 | — | — | 5.00 | — | — | 1.43 | — | — |
| Guar gum type AA | — | — | — | — | — | 3.0 | — | — | 6.0 | — | — | 6.0 |
| Menthol crystals | — | — | — | — | — | — | — | — | — | 1.43 | — | — |
| Polyoxyalkylene block copolymer[12] | — | — | — | — | — | — | — | — | — | 5.00 | — | — |

[1] A-coating composition of the non-adhesive reservoir layer.
[2] M-coating composition of the water-impermeable barrier layer.
[3] B-coating composition of the hydrating mucoadhesive base layer.
[4] CAB 381-2 from FMC Corp., a commercially available cellulose acetate butyrate.
[5] Plasdone K-90 from GAF Corp., a commercially available polyvinyl pyrrolidone.
[6] Ethyl acetate:acetone:isopropanol in a weight ratio of 5:4:1, respectively.
[7] Eastman ® SAIB-90 from Eastman Chemical Products, Inc., Kingston, TN, a commercially available sucrose acetate isobutyrate.
[8] FD&C Lake from Coloron, Inc., commercially available colorants.
[9] Carbopol ® Ex55 from B.F. Goodrich Corp., a commercially available polycarbophil.
[10] Kalacid ® from Kelco, Div. of Merck, Inc., a commercially available alginic acid.
[11] Illustrative flavorings include peppermint oil, spearmint oil and the like.
[12] Pluronic ® F-68 from BASF Wayandotte Corporation, Parsippany, N.J., a commercially available polyoxyalkylene block copolymer.

The procedure for preparation of coating solutions for the mucoadhesive buccal dosage form was as follows. A mixture of the solvent solution was prepared. Cellulose acetate butyrate powder was added to the solvent solution under constant mixing as by a magnetic bar and stirrer assembly. Then the plasticizer such as acetylated monoglyceride or a sucrose acetate isobutyrate:ethanol solution in a weight ratio of about 9:1, respectively, was added. This was followed by the addition of semi-soluble ingredients and relatively insoluble ingredients such as polycarbophil, guar gum, titanium dioxide and FD & C color lake powders (pigment).

After the addition of all the components, the solids content was adjusted to a range of about 25 percent to about 60 percent with the incorporation of additional solvent solution as needed. Each coating solution was degassed using an ultra-sonic bath.

Film coating was performed using a model SV-1 coating and laminating equipment (Werner-Mathis USA, Inc., Concord, North Carolina). A suitable release liner, such as Scotchpak ® 1361 made by 3M Company (St. Paul, Minnesota), or 1726D PET Silox made by Akrosil, was used to cast the film using a roller doctor knife assembly of the equipment. The coating composition of the non-adhesive reservoir layer (A) was wet coated on a piece of release liner approximately 12 inches by 13 inches with the knife slit set at 0.5 millimeters. After partial air drying in a laboratory hood, the semi-dry film was coated with the coating composition of the water-impermeable barrier layer (M) to bond the barrier layer to the reservoir layer. The knife slit was set at 0.6 millimeters for application of the barrier layer. Similarly, after partial air drying of the barrier layer in the hood, the coating composition of the hydrating mucoadhesive base layer (B) of the trilaminate film was coated on with the knife slit set at 0.6 millimeters. The trilaminate film was then air dried overnight in a hood at ambient temperature. Thin, circular samples having a surface area of approximately 0.50 and approximately 1.33 square centimeters and a thickness of approximately 0.30 millimeters were die cut manually and packaged in suitable containers.

EXAMPLE 2:

Mucoadhesive buccal dosage forms containing dental care agents.

Mucoadhesive buccal dosage forms having the composition illustrated in TABLE II, below, were prepared using the procedure and equipment described in EXAMPLE 1. The dental care agent was added subsequent to the addition of the plasticizer. After drying, the trilaminate film was die cut to obtain thin circular buccal dosage forms for application to the buccal mucosa. The distinction of the two sides, one off-white in color and one color-coded, provide an easy means of identifying the side off-white in color as the side to be positioned on the buccal mucosa. In test applications with laboratory volunteers, the forms remained in place for a time period of over of 6 hours after application, thus providing a sustained release of flavor and dental care agent into the buccal cavity. The test films did not curl up during the entire period of application.

TABLE II

Mucoadhesive Buccal Dosage Form Compositions For Sustained Delivery Containing Dental Care Agents

| Component | Dosage Form Compositions C5 | | | | | |
|---|---|---|---|---|---|---|
| | A[1] | | M[2] | | B[3] | |
| | Wt (g) | Wt %[4] | Wt (g) | Wt %[4] | Wt (g) | Wt %[4] |
| Cellulose acetate butyrate[5] | 3.25 | 16.71 | 7.0 | 67.31 | 2.0 | 20 |
| Triacetin | 2.00 | 10.28 | — | | 1.0 | 10 |
| Polycarbophil[6] | — | | — | | 6.0 | 60 |
| Polyvinyl pyrrolidone[7] | 2.00 | 10.28 | — | | 1.0 | 10 |
| Solvent solution[8] | 30.00 | | 30.0 | | 30.0 | |
| Colorant[9] | 0.01 | 0.05 | — | | — | |
| Titanium (IV) dioxide | — | | 2.0 | 19.23 | — | |
| Sucrose acetate isobutyrate[10] | — | | 1.4 | 13.46 | — | |
| Alginic acid[11] | 7.00 | 35.98 | — | | — | |
| Flavoring[12] | 5.00 | 25.70 | — | | — | |
| Dental care agent[13] | 0.1926 | 1.00 | — | | — | |

[1]A-coating composition of the non-adhesive reservoir layer.
[2]M-coating composition of the water-impermeable barrier layer.
[3]B-coating composition of the hydrating mucoadhesive base layer.
[4]Based on the total weight of the non-solvent components.
[5]CAB 381-2 from FMC Corp., a commercially available cellulose acetate butyrate.
[6]Carbopol ® Ex 55 from B.F. Goodrich Corp., a commercially available polycarbophil.
[7]Plasdone K-90 from GAF Corp., a commercially available polyvinyl pyrrolidone.
[8]Ethyl acetate:acetone:isopropanol in a weight ratio of 5:4:2, respectively.
[9]FD & C Lake from Coloron, Inc., a commercially available colorants.
[10]Eastman ® SAIB-90 from Eastman Chemical Products, Inc., Kingston, Tennessee, a commercially available sucrose acetate isobutyrate.
[11]Kalacid ® from Kelco, Division of Merck, Inc., a commercially available alginic acid.
[12]Illustrative flavorings include peppermint oil, spearmint oil and the like.
[13]Illustrative dental care agents include chlorohexidine, chlorobutanol, chlorothymol, cetrimonium bromide and the like.

EXAMPLE 3:

Mucoadhesive buccal dosage forms containing systemic therapeutic agents.

Mucoadhesive buccal dosage forms having the compositions illustrated in Table III, below, were prepared using the procedure and equipment described in EXAMPLE 1.

TABLE III

Mucoadhesive Buccal Dosage Form Compositions Containing Therapeutic Agents In A Mucoadhesive Layer for Sustained Systemic Delivery

| Component, (grams) | C6 | | | C7 | | | C8 | | |
|---|---|---|---|---|---|---|---|---|---|
| | A[1] | M[2] | B[3] | A[1] | M[2] | B[3] | A[1] | M[1] | B[3] |
| Triacetin | 2.00 | — | 2.00 | 2.00 | — | 2.00 | 2.00 | — | 2.00 |
| Solvent solution[4] | 30.00 | 30.00 | 30.00 | 30.00 | 30.00 | 30.00 | 30.00 | 30.00 | 30.00 |
| Colorant[5] | 0.01 | — | — | 0.01 | — | — | 0.01 | — | — |
| Titanium dioxide | — | 2.00 | — | — | 2.00 | — | — | 2.00 | — |
| Sucrose acetate isobutyrate[6] | — | 1.40 | — | — | 1.40 | — | — | 1.40 | — |
| Alginic acid[7] | 7.00 | — | — | 7.00 | — | — | 7.00 | — | — |
| Flavoring[8] | 5.00 | — | — | 5.00 | — | — | 5.00 | — | — |
| Cellulose acetate butyrate[9] | 3.25 | 7.0 | 2.00 | 3.25 | 7.0 | 2.00 | 3.25 | 7.0 | 4.00 |
| Polycarbophil[10] | — | — | 3.00 | — | — | 5.00 | — | — | 3.00 |
| Polyvinyl pyrrolidone[11] | 2.00 | — | — | 2.00 | — | 1.00 | 2.00 | — | — |
| Polyethylene glycol 800 | — | — | 1.00 | — | — | — | — | — | 2.00 |
| Guar gum, Type AA | — | — | 3.00 | — | — | — | — | — | 3.00 |
| 17-βestradiol | — | — | 1.00 | — | — | — | — | — | — |
| Albuterol | — | — | — | — | — | 4.00 | — | — | — |

TABLE III-continued

Mucoadhesive Buccal Dosage Form Compositions Containing Therapeutic Agents In A Mucoadhesive Layer for Sustained Systemic Delivery

| Component, (grams) | C6 | | | C7 | | | C8 | | |
|---|---|---|---|---|---|---|---|---|---|
| | $A^1$ | $M^2$ | $B^3$ | $A^1$ | $M^2$ | $B^3$ | $A^1$ | $M^1$ | $B^3$ |
| Nifedipine | — | — | — | — | — | — | — | — | 4.00 |

[1] A-coating composition of the non-adhesive reservoir layer.
[2] M-coating composition of the water-impermeable barrier layer.
[3] B-coating composition of the hydrating mucoadhesive base layer.
[4] Ethyl acetate:acetone:isopropanol in a weight ratio of 5:4:1, respectively.
[5] FD & C Lake from Coloron, Inc., commercially available colorants.
[6] Eastman ® from Eastman Chemical Products, Inc., Kingston, Tennessee, a commercially available sucrose acetate isobutyrate.
[7] Kalacid ® from Kelco, Division of Merck, Inc., a commercially available alginic acid.
[8] Illustrative flavorings include peppermint oil, spearmint oil and the like.
[9] CAB 381-2 from FMC Corp., a commercially available cellulose acetate butyrate.
[10] Carbopol ® Ex 55 from B.F. Goodrich Corp., a commercially available polycarbophil.
[11] Plasdone K-90 from GAF Corp., a commercially available polyvinyl pyrrolidone.

The therapeutic agent was added subsequent to the plasticizer. After drying, the trilaminate film was die cut to obtain thin circular buccal dosage forms. One side of the form was off-white in color and contained the therapeutic agent for systemic delivery and the mucoadhesive. The other side was color-coded and did not adhere to the mucosa. Sustained release of flavor and the therapeutic agent was obtained. No curling of the buccal dosage after application to the buccal mucosa for a prolonged period of time was observed.

This invention has been described in terms of specific embodiments set forth in detail, but it should be understood that these are by way of illustration only and that the invention is not necessarily limited thereto. Modifications and variations will be apparent from this disclosure and may be resorted to without departing from the spirit of this invention, as those skilled in the art will readily understand. Accordingly, such variations and modifications of the disclosed products are considered to be within the purview and scope of this invention and the following claims.

We claim:

1. A buccal dosage form suitable for delivery of an active ingredient in a buccal cavity and comprising:
   a hydratable mucoadhesive base layer;
   a non-adhesive reservoir layer; and
   a water-impermeable barrier sandwiched between and bonded to said base layer and said reservoir layer;
   said reservoir layer comprising a plasticized film-forming cellulose ester, a dehydrated hydrogel and said active ingredient to be dispersed directly into the buccal cavity; and
   said water-impermeable barrier comprising a cellulose ester film.

2. The buccal dosage form in accordance with claim 1 wherein the mucoadhesive base layer is constituted by a member of the group consisting of water-swellable, but water-insoluble, fibrous, cross-linked carboxy-functional polymers, hydrophilic polysaccharide gums, cross-linked alignate gum gels, water-dispersible polycarboxylated vinyl polymers, and mixtures thereof.

3. The buccal dosage form in accordance with claim 2 wherein the hydrophilic polysaccharide gum is a member of the group consisting of a natural plant exudate and a seed gum.

4. The buccal dosage form in accordance with claim 2 wherein the hydrophilic polysaccharide gum is a member of the group consisting of karaya gum, ghatti gum, locust bean gum, guar gum, psillium seed gum and mixtures thereof.

5. The buccal dosage form in accordance with claim 1 wherein the cellulose ester film is a member of the group comprising of cellulose acetate butyrate, cellulose acetate isobutyrate, and cellulose acetate propionate.

6. The buccal dosage form in accordance with claim 1 wherein the weight ratio of cellulose ester to dehydrated hydrogel in the reservoir layer is in the range of about 7:3 to about 1:4, respectively.

7. The buccal dosage form in accordance with claim 1 wherein the weight ratio of cellulose ester to dehydrated hydrogel in the reservoir layer is in the range of about 6:4 to about 1:3, respectively.

8. The buccal dosage form in accordance with claim 1 wherein the hydrogel is a combination of a polyoxyalkylene block copolymer and alginic acid.

9. The buccal dosage form in accordance with claim 8 wherein the weight ratio of polyoxyalkylene block copolymer to alginic acid is about 5 to about 0.2, respectively.

10. The buccal dosage form in accordance with claim 8 wherein the polyoxyalkylene block copolymer contains oxyethylene chains and oxypropylene chains in a weight ratio of about 7:3, respectively.

* * * * *